United States Patent [19]

Knifton

[11] 4,315,994
[45] Feb. 16, 1982

[54] PREPARATION OF GLYCOLS AND ETHERS

[75] Inventor: John F. Knifton, Austin, Tex.

[73] Assignee: Texaco Inc., White Plains, N.Y.

[21] Appl. No.: 220,486

[22] Filed: Dec. 29, 1980

[51] Int. Cl.$^3$ ............................................. C07C 27/06
[52] U.S. Cl. .................................... 518/701; 518/700; 252/131 R
[58] Field of Search ................................. 518/700, 701

[56] References Cited

U.S. PATENT DOCUMENTS

| | | | |
|---|---|---|---|
| 4,136,104 | 1/1979 | Hwang | 518/715 |
| 4,265,828 | 5/1981 | Knifton | 518/700 |

Primary Examiner—Howard T. Mars
Attorney, Agent, or Firm—Carl G. Ries; Jack H. Park; Walter D. Hunter

[57] ABSTRACT

This invention concerns a process of making alkylene glycols and their ethers which comprises contacting a mixture of carbon monoxide and hydrogen with a bimetallic catalyst system comprising ruthenium(III) acetylacetonate and rhodium(III) acetylacetonate dispersed in a low melting quaternary phosphonium or ammonium base or salt at a pressure of 500 psi or greater and at a temperature of at least 150° C. for a sufficient time to provide said glycols and ethers.

12 Claims, No Drawings

PREPARATION OF GLYCOLS AND ETHERS

SUMMARY AND BACKGROUND OF THE INVENTION

This invention concerns an improved process for preparing alkylene glycols and their alkyl ethers by reaction of oxides of carbon with hydrogen in presence of a catalyst system.

There are even-increasing efforts to provide new methods of making ethylene glycol particularly useful as a component in polyester fiber and antifreeze formulations. An ever present aim is to prepare said glycol in relatively high yields involving a catalyst system providing good selectivity.

One proposed mode of making ethylene glycol is the reaction of carbon monoxide and hydrogen in presence of variously proposed catalyst systems. The mixture of carbon monoxide and hydrogen, commonly known as synthesis gas, is reacted at elevated pressures and temperatures. For example, in Belgium patent No. 793,086 and U.S. Pat. No. 3,940,432 there is described the co-synthesis of methanol and ethylene glycol from mixtures of carbon monoxide and hydrogen using a complex rhodium catalyst. While other metals of group VIII of the Periodic Table have been tested for activity under similar conditions, including cobalt, ruthenium, copper, manganese, iridium and platinum, only cobalt was found to have slight activity. The use of ruthenium compounds in particular failed to produce polyfunctional products such as ethylene glycol. This is illustrated in U.S. Pat. No. 3,833,634 for solution of triruthenium dodecarbonyl.

This invention therefore is to provide a process of making alkylene glycols and their ethers utilizing a highly effective catalyst system which produces said glycols and ethers in good yields and selectivity. Advantageously with the catalyst system of this invention hydrocarbon formation during the course of the reaction is largely avoided and the catalyst system itself can be recycled to the process while maintaining a high degree of activity.

SUMMARY OF THE INVENTION

This invention concerns a method for making alkylene glycols as exemplified by ethylene glycol and propylene glycol and their ethers which comprises contacting a mixture of CO and $H_2$ with a bimetallic catalyst system dispersed in a low melting quaternary phosphonium or ammonium base or salt at a pressure of 500 psi or greater and at a temperature of at least 150° C. for a sufficient time to provide said glycols and ethers.

DETAILED DESCRIPTION OF THE INVENTION

In the narrower and more preferred practice of this invention alkylene glycols and glycol monoalkylethers are prepared concurrently from a synthesis gas mixture of carbon monoxide and hydrogen by a process which comprises contacting said mixture of carbon monoxide and hydrogen with a bimetallic catalyst system composed of a ruthenium(III) acetylacetonate and rhodium-(III) acetylacetonate dispersed in a low melting quaternary phosphonium base or salt of an organic or mineral acid at a temperature of between 180° and 250° C., and at superatmospheric pressures of 2000 psi or greater until substantial formation of the desired ethylene glycol, propylene glycol and glycol monoalkylethers has been achieved.

Recovery of the alkylene glycols and glycol monoalkylethers from the reaction product can be carried out in any convenient or convential manner such as by distillation, extraction, etc.

The bimetallic catalyst systems suitable for the practice of this invention comprise ruthenium(III) acetylacetonate and rhodium(III) acetylacetonate dispersed in a quaternary base or salt. The catalyst systems of this invention give higher yields of glycols and glycol ethers than can be obtained when the catalyst utilized is solely a ruthenium compound dispersed in the quaternary base or salt. Furthermore, the product mixtures contain significant quantities of useful propylene glycol, but little unwanted hydrocarbon (methane). Also the stability of this catalyst system, as previously pointed out, is such that it can be conveniently recovered from the reaction mixture and recycled to the process.

Generally the catalyst system will contain from about 20 to about 80 mole percent of ruthenium(III) acetylacetonate with the balance being rhodium(III) acetylacetonate based on the total number of moles of the ruthenium compound and of the rhodium compound in the system. Preferably, the catalyst system will contain about equimolar amounts of the ruthenium and rhodium compounds.

The ruthenium-containing compound and the rhodium-containing compound are prior to their catalytic use in making alkylene glycols, first dispersed in a low melting quaternary phosphonium or ammonium base or salt. It is interesting to note that the ruthenium(III) acetylacetonate or the rhodium(III) acetylacetonate alone, without being dispersed in said salt or base, have little if any activity in promoting the manufacture of ethylene or propylene glycol from synthesis gas.

The quaternary phosphonium or ammonium base or salt must be relatively low melting, that is, melt at a temperature less than about the temperature of reaction of making ethylene glycol. Usually the quaternary compound has a melting point less than about 180° C., and most often has a melting point less than 150° C.

Suitable quaternary phosphonium salts have the formula:

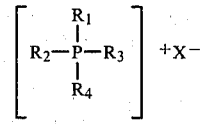

where $R_1$, $R_2$, $R_3$ and $R_4$ are organic radicals, particularly alkyl, aryl or alkaryl radicals bonded to the phosphorous atom, and X is an anionic species. The organic radicals useful in this instance include those alkyl radicals having 1 to 20 carbon atoms in a branched or linear alkyl chain; they include, for example, the methyl, ethyl, n-butyl, iso-butyl, octyl, 2-ethylhexyl and dodecyl radicals.

Tetraoctylphosphonium bromide and tetrabutylphosphonium bromide are typical examples presently in commercial production. The corresponding quaternary phosphonium and ammonium acetates, hydroxides, nitrates, chromates, tetrafluoroborates and other halides, such as the corresponding chlorides, and iodides, are also satisfactory in this instance. Also useful are the correspounding quaternary ammonium bases and salts of the above series of compounds.

Equally useful are the phosphonium and ammonium salts containing phosphorus or nitrogen bonded to a mixture of alkyl, aryl and alkaryl radicals. Said aryl and alkaryl radicals may each contain 6 to 20 carbon atoms. The aryl radical is most commonly phenyl. The alkaryl group may comprise phenyl substituted with one or more $C_1$-$C_{10}$ alkyl substituents, bonded to the phosphorus or nitrogen atom through the aryl function.

Illustrative examples of suitable quaternary phosphonium and ammonium bases and salts include tetrabutylphosphonium bromide, tetraoctylphosphonium bromide, heptyltriphenylphosphonium bromide, tetrabutylphosphonium iodide, tetrabutylphosphonium chloride, tetrabutylphosphonium nitrate, tetrabutylphosphonium hydroxide, tetrabutylphosphonium chromate, tetrabutylphosphonium tetrafluoroborate, tetrabutylphosphonium acetate, tetrabutylammonium bromide and tetramethylammonium hydroxide, pentahydrate and trimethyldodecylammonium bromide.

The preferred quaternary salts are generally the tetralkylphosphonium salts containing alkyl groups having 3-8 carbon atoms, such as butyl, hexyl and octyl. Tetrabutylphosphonium salts, such as tetrabutylphosphonium bromide, are most preferred for the practice of this invention.

Preferred tetrabutylphosphonium salts or bases include the bromide, chloride, iodide, acetate, the chrome salts and hydroxide base.

The quantity of ruthenium catalyst (exclusive of quaternary salt) employed in the instant invention is not critical and may vary over a wide range. In general, the novel process is desirably conducted in the presence of a catalytically effective quantity of the active ruthenium species and of the active rhodium species which gives the desired products in reasonable yields. The reaction proceeds when employing as little as about $1 \times 10^{-6}$ weight percent, and even lesser amounts, of ruthenium together with about $1 \times 10^{-6}$ weight percent or less of rhodium, basis the total weight of the reaction mixture. The upper concentration is dictated by a variety of factors including catalyst cost, partial pressures of carbon monoxide and hydrogen, operating temperature etc. A ruthenium concentration of from about $1 \times 10^{-5}$ to about 5 weight percent in conjunction with a rhodium concentration of from about $1 \times 10^{-5}$ to about 5 weight percent, based on the total weight of reaction mixture is generally desirable in the practice of this invention.

The temperature range which can usefully be employed in these syntheses is a variable dependent upon other experimental factors, including the pressure, and the concentration and choice of a particular species of ruthenium catalyst among other things. The range of operability is from about 150° to 350° C. when superatmospheric pressure of syngas are employed. A narrow range of 180°-250° C. represents the preferred temperature range.

Superatmospheric pressures of 500 psi or greater lead to substantial yields of ethylene glycol by the process of this invention. A preferred operating range is from 2000 psi to 9000 psi, although pressures above 9000 psi also provide useful yields of desired glycol.

The relative amounts of carbon monoxide and hydrogen which may be initially present in the syngas mixture can be varied widely. In general, the mole ratio of CO-to-$H_2$ is in the range from about 20:1 up to about 1:20, preferable from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether, alkanols such as methanol and acid esters such as methyl acetate.

Ethylene glycol and propylene glycol derivatives may also be formed while carrying out the process of this invention. Most often these derivatives are ethylene glycol monoalkylethers, they typically include ethylene glycol monoethyl ether, ethylene glycol monoethyl ether and ethylene glycol monopropyl ether or the corresponding propylene glycol derivatives. If the low melting quaternary ammonium or phosphonium salt employed is a carboxylic acid salt, the crude liquid product mixture may also contain significant quantities of ethylene glycol acid esters, particularly ethylene glycol mono and diesters.

The major by-products of these glycol syntheses are most commonly methanol, ethanol and n-propanol, which are, of course, also useful compounds and major articles of commerce. The alkanols, ethylene glycol, propylene glycol and their monoalkyl ethers can easily be separated from one another by conventional means, e.g. fractional distillation in vacuo.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired glycol product, and said material may be recovered by methods well known in the art, such as distillation, fractionation, extraction and the like. A fraction rich in ruthenium catalyst components may then be recycled to the reaction zone, if desired, and additional products generated.

The products have been identified in this work by one or more of the following analytical procedures, viz, gas-liquid phase chromatograph (GLC), infrared (IR), mass spectrometry, nuclear magnetic resonance (nmr) and elemental analyses, or a combination of these techniques. Analyses have, for the most part, been by parts in weight; all temperatures are in degrees centigrade and all pressures in pounds per square inch gauge (psi).

The following examples illustrate the novel process of this invention.

EXAMPLE 1

A mixture of ruthenium(III) acetylacetonate (4 mmole, 1.594 g) and rhodium(III) acetylacetonate (2 mmole, 0.800 g) dispersed in tetrabutylphosphonium bromide (15 g, 44.2 mmole, m.p. −100° C.) was transferred in a glass liner to the 850 ml pressure reactor equipped with heating and means of agitation. The reactor was sealed, flushed with a gaseous mixture containing equal molar amounts of carbon monoxide and hydrogen and pressured to 2000 psi with the same gaseous mixture. The mixture was heated to 220° C. with rocking, the pressure was raised to 6300 psi by addition of the carbon monoxide-hydrogen mixture from a large surge tank and the reactors held at temperature for 18 hrs. Pressure in the reactor was maintained at ca. 6300 psi by incremental additions of the carbon monoxide-hydrogen mixture from the surge tank.

On cooling, the reactor pressure (3300 psi) was noted, a typical gas sample was taken and the excess gas removed. A reddish-brown liquid product (50.2 g) was analyzed by GLC and Karl Fischer titration. The liquid yield increase was 189 weight percent (calcd. (50.2−17.4)×100%).

Analysis of the liquid product showed the presence of:

14.6 wt% ethylene glycol
17.2 wt% ethylene glycol monoalkyl ethers
1.2 wt% propylene glycol
23.6 wt% ethanol
24.4 wt% methanol
1.2 wt% water The ethylene glycol, propylene glycol and glycol ethers were recovered from the crude liquid product by fractional disillation in vacuo. Distillate fractions typically showed an ethylene glycol content of ↓80%. Upon cooling, the residual catalyst dispersed in tetrabutyl-phosphonium bromide was recovered as a dark-red crystalline solid (15.5 g) having a m.p. of ca 90° C.

EXAMPLE 2

A mixture of ruthenium(III) acetylacetonate (4 mmole) and rhodium(III) acetylacetonate (2 mmole) dispersed in tetrabutylphosphonium bromide (10 g) was transferred in a glass liner to the 450 ml pressure reactor. Said reactor was sealed, flushed with a gaseous mixture containing equal molar amounts of carbon monoxide and hydrogen and pressured to 4000 psi with the same gaseous mixture. The mixture was heated to 220° C. with rocking, and the reactor held at temperature for 18 hr.

On cooling, the reactor pressure (1960 psi) was noted, a gas sample was taken, and the excess gas removed. A deep-red liquid product (22.5 g) was recovered from the reactor. The liquid yield increase was 81%.

Analysis of the liquid product by GLC showed the presence of:

10.0 wt% ethylene glycol
18.4 wt% glycol ethers
31.6 wt% ethanol
15.7 wt% methanol
1.0 wt% propylene glycol
1.2 wt% water The ethylene glycol, propylene glycol, glycol ethers and water were recovered from the crude liquid product together with the ethanol and methanol by fractional distillation in vacuo. Upon cooling, the residual catalyst dispersed in tetrabutylphosphonium bromide was recovered as a dark-red crystalline solid.

COMPARATIVE EXAMPLE 3

In this comparative example the experimental procedure of Example 2 was followed. The reactor was charged with rhodium(III) acetylacetone dispersed in tetrabutylphosphonium bromide (10.0 g). No ruthenium was present in this run. After pressuring the reactor to 4000 psi with an equal molar mixture of carbon monoxide and hydrogen and heating to 220° C. for 18 hrs, the reactor was cooled rapidly and the residual pressure (3680 psi) was noted. Excess gas was removed by depressuring and the dark brown viscous liquid product (12.1 g) recovered from the glass reactor liner.

The liquid product resolidified upon cooling and GLC analysis did not show the presence of significant (less than 1%) quantities of ethylene glycol. The liquid yield weight increase was only 12%.

COMPARATIVE EXAMPLES 4–5

Table I gives the results obtained in the Comparative Examples 4 and 5 in which the catalyst employed was ruthenium(III) acetylacetonate alone dispersed in tertabutylphosphonium bromide and the procedure was similar to that outlined in Example 1. No rhodium was present in these runs.

The exemplified data showed that the combined yields of glycol plus glycol ethers was significantly lower than that achieved with the Ru-Rh bimetallic catalyst combination. Furthermore, no propylene glycol was detected in the reaction mixtures.

TABLE I

| Example[a] | CATALYST COMPOSITION | | | Liquid Yield Increase (%) | LIQUID PRODUCT COMPOSITION (WT %) | | | | | | | | |
|---|---|---|---|---|---|---|---|---|---|---|---|---|---|
| | Ruthenium Source | Quaternary Salt | mp. | | H₂O | MeOH | EtOH | PrOH | EGMME[b] | EG[c] | PG[d] | EGMEE[e] | EGMPrE[f] |
| 4 | Ru(Acac)₃ | Bu₄PBr | 100° | 186 | 1.5 | 26.1 | 33.4 | 5.0 | 9.7 | 5.6 | — | 6.5 | 1.4 |
| 5[g] | Ru(Acac)₃ | Bu₄PBr | 100° | 116 | 1.8 | 35.3 | 22.8 | 2.7 | 7.4 | 9.5 | — | 4.1 | 1.1 |

[a]Operating conditions: 8 mmole Ru; 30 g Bu₄PBr; 1:1 CO/H₂ syngas; ca 6300 psi constant pressure, 220° C., 18 hr.
[b]EGMME = Ethylene glycol monomethyl ether.
[c]EG = Ethylene glycol
[d]PG = Propylene glycol
[e]EGMEE = Ethylene glycol monoethyl ether.
[f]EGMPrE = Ethylene glycol monopropyl ether.
[g]4 mmole Ru; 15 g Bu₄PBr; 6 hr.

COMPARATIVE EXAMPLE 6

In this comparative example the experimental procedure of Example 2 was followed. The reactor was charged with rhodium(III) acetylacetonate (1 mmole) and ruthenium(III) acetylacetonate (2 mmole). No tetrabutylphosphonium bromide was present in this run. After pressuring the reactor to 4000 psi with an equal molar mixture of carbon monoxide and hydrogen and heating to 220° C. for 18 hrs., the reactor was cooled rapidly and the reactor pressure (2610 psi) was noted. There was no liquid product present in the glass reactor liner.

EXAMPLE 7

Following the procedures of Example 1, the reactor was charged with a mixture of ruthenium(III) acetylacetonate (2 mmole) and rhodium(III) acetylacetonate (2 mmole) dispersed in tetrabutylphosphonium bromide (15 g, 44.2 mmole).

After reaction, the deep-red liquid product (41.2 g) was analyzed by GLC and Karl Fischer titration. The liquid yield increase was 148%. Analysis of the liquid product showed the presence of:
- 16.1 wt% ethylene glycol
- 15.4 wt% ethylene glycol monoalkyl ethers
- 0.6 wt% propylene glycol
- 24.2 wt% ethanol
- 25.1 wt% methanol
- 1.5 wt% water Typical off-gas samples showed the presence of:
- 42.6% hydrogen
- 42.5% carbon monoxide
- 9.2% carbon dioxide
- 1.4% methane

EXAMPLE 8

Following the procedures of Example 1, the reactor was charged with a mixture of ruthenium(III) acetylacetonate (1 mmole) and rhodium(III) acetylacetonate (2 mmole) dispersed in tetrabutylphosphonium bromide (7.5 g, 22 mmole).

After reaction, the reddish-brown liquid product (22.5 g) was analyzed by GLC and Karl Fischer titration. The liquid yield increase was 159%. Analysis of the liquid product showed the presence of:
- 18.5 wt% ethylene glycol
- 12.0 wt% ethylene glycol monoalkyl ethers
- 1.6 wt% propylene glycol
- 19.3 wt% ethanol
- 27.8 wt% methanol
- 2.9 wt% water Typical off-gas samples showed the presence of:
- 42.0% hydrogen
- 44.7% carbon monoxide
- 9.9% carbon dioxide
- 1.6% methane

EXAMPLE 9

Following the procedures of Example 1, the reactor was charged with a mixture of ruthenium(III) acetylacetonate (4 mmole) and rhodium(III) acetylacetonate (2 mmole) dispersed in heptyltriphenylphosphonium bromide (15 g, 33.8 mmole).

After reaction, the two-phase liquid product (24.5 g) was analyzed by GLC and Karl Fischer titration. The liquid yield increase was 41%. Analysis of the major fraction of the product liquid showed the presence of:
- 12.5% ethanol
- 12.3% n-proponal
- 1.9% methanol
- 9.5% ethylene glycol monoalkyl ethers
- 1.6% ethylene glycol
- 5.2% water

EXAMPLE 10

Following the procedures of Example 1, the reactor was charged with a mixture of ruthenium(III) acetylacetonate (2 mmole) and rhodium(III) acetylacetonate (2 mmole) dispersed in tetrabutylphosphonium iodide (15.0 g, 38.8 mmole).

After reaction, the deep-red liquid product (52.2 g) was analyzed by GLC and Karl Fischer titration. The liquid yield was 214%. Analysis of the liquid product showed the presence of:
- 14.0 wt% ethylene glycol
- 10.5 wt% ethylene glycol monoalkyl ether 1.2 wt% propylene glycol
- 30.6 wt% ethanol
- 28.0 wt% methanol
- 2.6 wt% water The ethylene glycol, propylene glycol and glycol monoalkyl ether product fraction were recovered from the crude liquid product mixture by fractional distillation in vacuo. Heavier product fractions typically displayed an ethylene glycol plus propylene glycol content of >90%.

Upon cooling, the residual Ru-Rh catalyst dispersed in tetrabutylphosphonium bromide was recovered as a dark solid residue (16.0 g). This material was returned to the pressure reactor in the glass liner and CO hydrogenation was conducted as outlined in Example 1. After reaction, the crude liquid product was subject to GLC and Karl Fischer analysis, and fractionally distilled in vacuo.

Recycling of the original Ru-Rh/Bu4PI catalyst was conducted three times. Typical ethylene glycol, glycol monoalkyl ether production, and total liquid yields for this four cycle experiment as summarized in Table II.

TABLE II

| Ru + Rh/Bu4PI Catalyst Cycle | LIQUID PRODUCT COMPOSITION (WT%) | | |
|---|---|---|---|
| | Ethylene Glycol Content | Ethylene Glycol + Glycol Monoalkyl ether | Liquid Yield Increase(%) |
| 1 | 14.0 | 24.5 | 214 |
| 2 | 12.9 | 23.2 | 199 |
| 3 | 11.1 | 19.0 | 189 |
| 4 | 9.4 | 15.3 | 170 |

After four cycles the solid residual catalyst was subjected to elemental analyses for key elements. Data are as follows:

| | Residual Catalyst After 4 cycles | Fresh Catalyst Ru(Acac)3 + Rh(Acac)3/Bu4PI |
|---|---|---|
| % Rhodium | 1.1 | 1.2 |
| % Ruthenium | 0.8 | 1.2 |
| % Phosphorus | 7.3 | 7.3 |
| % Iodide | 35.2 | 29.8 |

It was concluded that any significant losses of high-value rhodium are within the errors of the rhodium analysis method. The presence of tetrabutylphosphonium iodide in this residual catalyst sample was confirmed by IR spectroscopy.

It is claimed:

1. A process of making alkylene glycols and their ethers which comprises the steps of contacting a mixture of CO and H2 with a catalytically effective amount of a bimetallic catalyst system comprising a ruthenium(III) acetylacetonate and rhodium(III) acetylacetonate dispersed in a low melting quaternary phosphonium or ammonium base or salt at a pressure of 500 psi or greater and at a temperature of at least 180° C. for a sufficient time to provide said alkylene glycols and their ethers.

2. The process of claim 1 wherein the process is conducted at a temperature of from about 180°–250° C.

3. The process of claim 1 wherein the process is conducted at a pressure of 2000 psi to 9000 psi.

4. The process of claim 1 wherein said quaternary phosphonium salt has a melting point less than about 180° C.

5. The process of claim 1 wherein said quaternary is a tetraalkylphosphonium salt.

6. The process of claim 5 wherein said alkyl groups contain 1–6 carbon atoms.

7. The process of claim 1 wherein said quaternary is a mixed alkyl-aryl phosphonium quaternary.

8. The process of claim 1 wherein said quaternary is a tetrabutylphosphonium salt.

9. The process of claim 8 wherein said tetrabutylphosphonium salt is selected from the group consisting of tetrabutylphosphonium bromide, tetrabutylphosphonium chloride, and tetrabutylphosphonium iodide.

10. The process of claim 8 wherein said quaternary phosphonium salt is tetrabutylphosphonium bromide.

11. The process of claim 1 wherein the said bimetallic catalyst system contains from about 20 to about 80 mole percent of ruthenium(III) acetylacetonate with the balance being rhodium(III) acetylacetonate based on the total number of moles of the ruthenium compound and the rhodium compound in the said system.

12. The process of claim 1 wherein the said bimetallic catalyst system contains equimolar amounts of the ruthenium and the rhodium compounds.

* * * * *